US 6,648,030 B1

(12) United States Patent
Sparks

(10) Patent No.: US 6,648,030 B1
(45) Date of Patent: Nov. 18, 2003

(54) STORAGE TANK VENTILATING AND STERILIZING SYSTEM

(76) Inventor: Robert J. Sparks, 1438 Juanita Ct., Upland, CA (US) 91786

( * ) Notice: Subject to any disclaimer, the term of this patent is extended or adjusted under 35 U.S.C. 154(b) by 0 days.

(21) Appl. No.: 10/202,115

(22) Filed: Jul. 25, 2002

(51) Int. Cl.[7] .......................... B65B 31/00; B01D 39/00
(52) U.S. Cl. ............................ 141/59; 141/11; 141/82; 141/67; 141/325; 96/224
(58) Field of Search ............................... 141/59, 11, 63, 141/64, 67, 69, 70, 82, 89, 91, 325; 422/121, 4, 24; 96/224, 223, 256, 243; 55/385.4; 454/173, 174, 183

(56) References Cited

U.S. PATENT DOCUMENTS 5,160,515 A * 11/1992 Nelson et al. ................. 96/224
6,562,106 B2 * 5/2003 Campbell ..................... 95/226

OTHER PUBLICATIONS

US2002/0121196 A1; Sep. 5, 2002; Thakur et al.*

* cited by examiner

Primary Examiner—Gregory Huson
Assistant Examiner—Khoa Huynh
(74) Attorney, Agent, or Firm—J. E. McTaggart

(57) ABSTRACT

A ventilating/sterilizing system for food-quality liquid storage tanks has a weatherproof overhead hood. Incoming air, drawn up into the hood is first filtered at the intake of an electric blower forcing the airflow through a main filter to be sterilized by ultraviolet radiation then heated for tank entry, where airflow drives out moisture and displaces air in the head region through a specially designed weather protective tank outlet vent with a removable cone-shaped dual-screen filter unit. A remote indicator light panel indicates normal operation and malfunctions. Stainless steel construction throughout minimizes deterioration and contamination. The main filter is enclosed in a housing mounted on a base unit containing the ultra-violet chamber, the heating chamber, and electrical components. The hood is hinged for intake filter access; similarly the blower assembly is hinged for main filter access for replacement or cleaning. Ultraviolet lamps in the base are accessible and replaceable from outside the unit without disassembly.

10 Claims, 3 Drawing Sheets

STORAGE TANK VENTILATING AND STERILIZING SYSTEM

FIELD OF THE INVENTION

The present invention relates to the field of sterile ventilating of food-quality liquid storage tanks to prevent contamination of tank contents and more particularly it relates to a continuous multi-step filtering, radiating and heating process and associated forced air apparatus for introducing warm sterilized air into the head space of a bulk liquid storage tank, including special outlet venting, in manner to prevent microorganism proliferation or other contamination of food products or ingredients stored in the tank.

BACKGROUND OF THE INVENTION

A storage tank for liquid food ingredients or products is subject to contamination, e.g. by bacterial multiplication, unless preventive measures are taken. In ordinary circumstances vacuum sealing is impractical in such tanks; typically they cannot be made and kept air free and sealed air tight. Sealing would create serious temperature and pressure related problems and would interfere with filling and emptying, so such tanks are normally vented. Even with tanks that are kept filled to capacity for long periods of time, there is typically some head space containing an amount of air which is subject to contamination. Then whenever any of the content is drawn off, the volume removed is replaced by atmospheric air entering through the vent system. Unless this replacement air is sterilized, it carries risk of contamination. Ordinary dust filters in the intake or the venting port are ineffective in filtering out harmful microorganisms.

Many conventional filters and associated mechanisms such as ductwork, blowers and motors, unless specially and properly designed, can actually harbor and nurture microorganisms that can enter and contaminate the tank. Positive prevention requires continuous, or at least frequent, introduction of sterilized air into the head space of the tank so as to purge and replace the accumulated head space air; the rate of air flow must be sufficient to more than keep up with the maximum rate of depletion or draw-off, otherwise subatmospheric pressure within the tank would tend to draw in potentially contaminated outside air.

DISCUSSION OF KNOWN ART

U.S. Pat. No. 5,358,009 to Cambell for a LIQUID STORAGE VESSEL VENTING SYSTEM discloses a system of check valves intended to selectively vent the tank by directing incoming air through a filter to remove airborne contaminants at an intake port and directing exhaust air through a separate outlet port.

U.S. Pat. No. 6,142,169 to Lees et al for a STERILE TANK VENTING SYSTEM FOR A FILLING MACHINE discloses a gas supply system including a sterile filter and a steam supply.

OBJECTS OF THE INVENTION

It is a primary object of the present invention to provide a method and associated facilities for fully sterilizing air and moving the sterilized air into the head space of a food-quality liquid storage tank for the prevention of contamination, particularly by microorganism invasion and proliferation.

It is a further object to provide a process of sequential steps including filtering, pressurizing and sterilizing in an optimal manner for introducing sterilized air into the head space of the tank.

It is a further object to provide a forced air sterilizer embodiment suitable for deployment in a food-quality liquid storage tank located in an outdoor environment.

It is a further object to configure a forced air filtering and sterilizing unit in a manner to facilitate cleaning, maintenance and replacement of components such as lamps and filters.

SUMMARY OF THE INVENTION

The foregoing objects have been met by the present invention of a liquid storage tank ventilation sterilizer that provides an overhead hood to minimize weather and environmental disturbances. Incoming air is first drawn in by an electric blower through an intake filter, then forced through a main filter. The airflow is then sterilized by ultraviolet radiation and then heated before entering the tank where it drives out moisture and stagnant air through a specially designed weather-protective outlet vent fitted with a removable cone shaped dual-screen filter unit. A remote indicator light panel indicates normal operation and provides warning of any malfunction.

BRIEF DESCRIPTION OF THE DRAWINGS

The above and further objects, features and advantages of the present invention will be more fully understood from the following description taken with the accompanying drawings in which.

DETAILED DESCRIPTION

Figure 1:
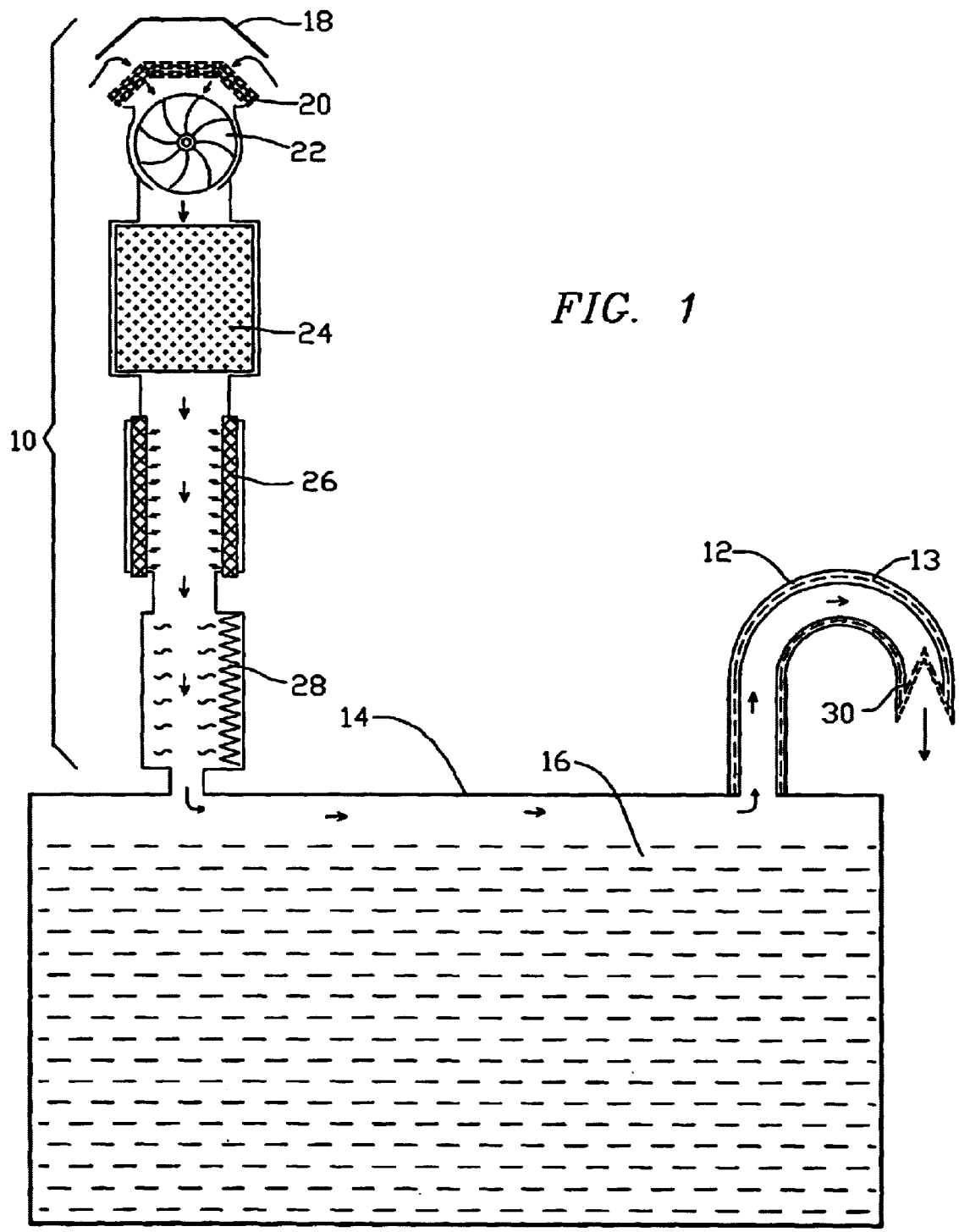
FIG. 1 is a functional block diagram illustrating in cross-section the process of the tank ventilation sterilizer of the present invention.

In FIG. 1, a functional block diagram, the several components shown in cross-section correspond to steps in the process of ventilating a storage tank with a sterilized air stream in accordance with the present invention The main intake assembly 10 and the outlet vent 12 are shown located near the opposite ends of a storage tank 14 containing liquid 16, which may be a food ingredient such as sucrose, glucose or high fructose, e.g. corn syrup, that needs to be protected against contamination, particularly bacterial proliferation, from the surrounding atmospheric air. Under a weather-protective hood 18, an intake filter 20, removes particulates greater than 10 microns from the incoming airstream, indicated by arrows, drawn through the intake filter 20 by a blower 22. The airstream output from blower 22 is directed downwardly through the main filter 24, through a UV (ultra-violet) chamber 26 and a heat chamber 28 from which hot sterilized air enters tank 14, driving out moisture and stagnant air through the outlet vent 12, thus reducing the potential for micro-organism and mold growth in the head space of tank 14.

At the outlet end of vent 12, a cone-shaped strainer 30 has two stainless steel layers, the upper having a mesh of 20/inch and the lower having a mesh of 80/inch. The cone shape of strainer 30 enables it to provide a ratio of 1½ to 1 open area to minimize airflow restriction, and is made to be easily removable and washable.

The curved, inverted U shape of vent 12 provides protection from the elements, e.g. wind and rain, and works as a natural air trap, preventing outside air from forcing its way back into the tank 14 even in the event of strong winds or failure of blower 22.

Vent 12 is made with an outer wall of aluminum tubing, typically four inches in diameter, and an inner wall of stainless steel, typically three inches in diameter, with a lining insulation 13 between the walls to prevent condensation, and is specially designed and arranged to avoid corners that in conventional air filter structures can become potential breeding centers for mold and other contamination.

Figure 2:
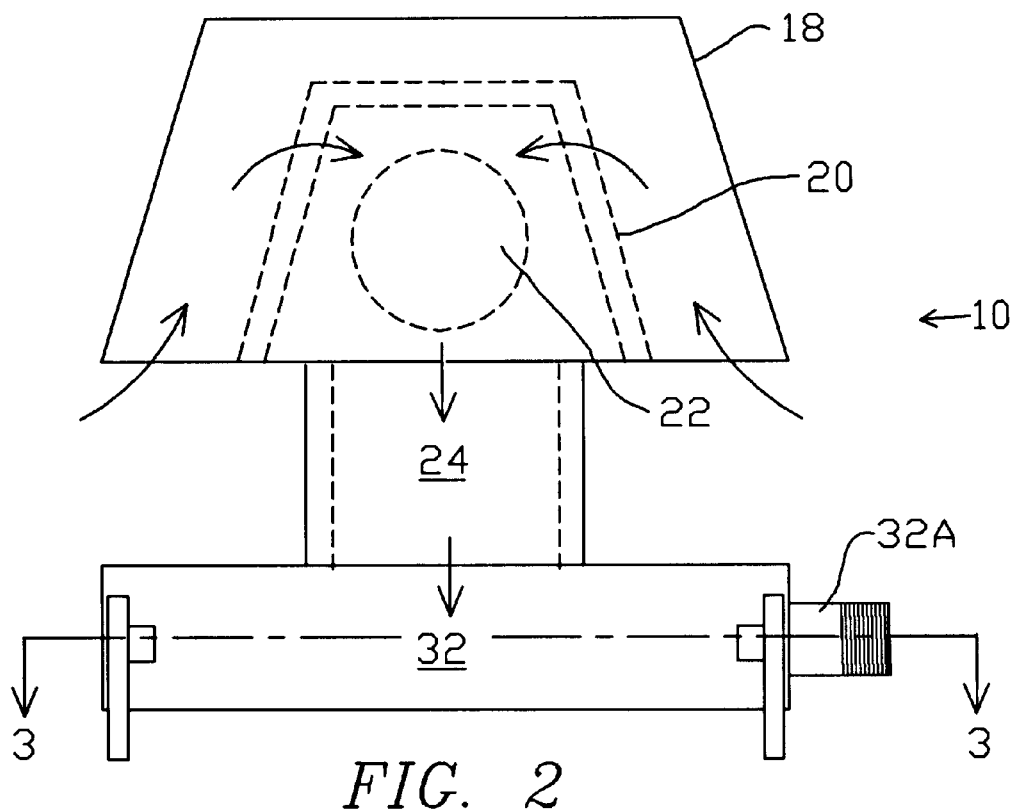
FIG. 2 is a simplified side elevational view of a tank ventilation sterilizer of the present invention.

In FIG. 2, a side elevational view of a tank ventilation sterilizer main intake assembly 10 illustrating a preferred embodiment of the present invention, airflow is shown by the arrows entering upwardly into protective hood 18, passing through intake filter 20 which is molded in the shape of an inverted cup as shown and serves to protect the blower 22 and its motor; taking the load off the main filter 24 it provides greater overall filter effectiveness and prolongs the main filter life.

Locating blower 22 and its motor between the intake filter 20 and the main filter 24 filters out contamination that is thrown off by the blower motor, a potential problem that is inherent in practically all blower motors.

Blower 22 forces the airstream downwardly into the cube-shaped main filter 24 which may be a mini-pleat type micro-filter manufactured by HEPA Corp., Anaheim, Calif. rated at 0.3 microns. From main filter 24 the airstream flows down into a modular base 32 for sterilization and heating.

Figure 3:
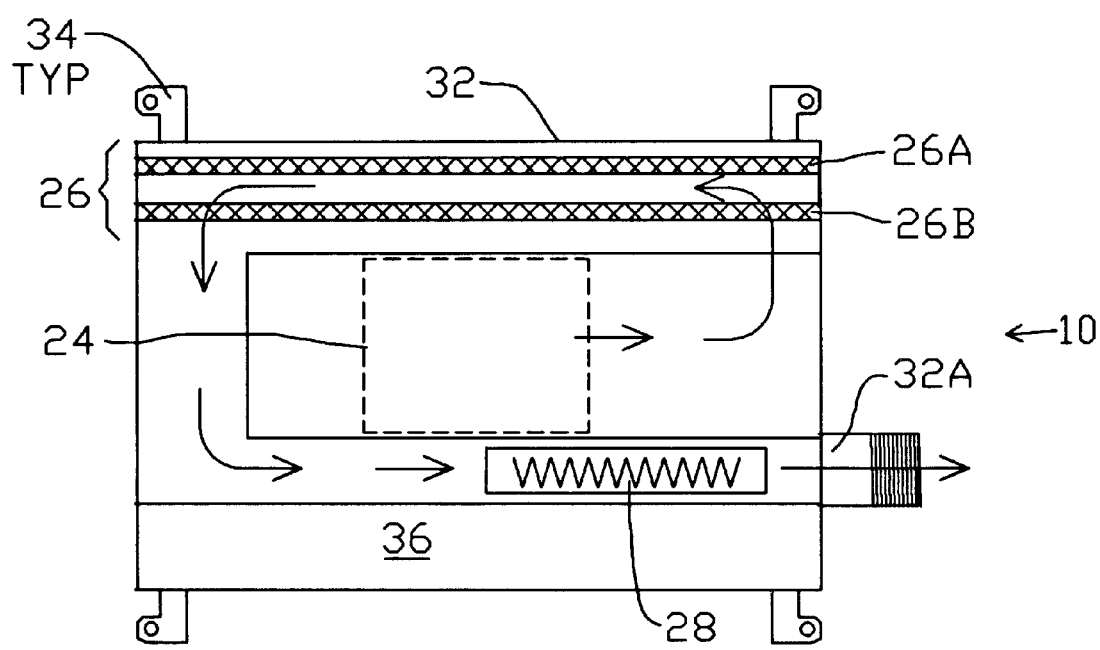
FIG. 3 is a cross-sectional view of the base portion at axis 3—3 of FIG. 2.

In FIG. 3, a cross-sectional view of base 32 taken at axis 3—3 of FIG. 2, the airstream, shown by arrows, from main filter 24, enters the radiation sterilizing chamber 26 where it is bathed in ultraviolet light between the pair of ultra-violet lamps 26A and 26B. These are enclosed in quartz sleeves and are arranged to be readily accessible and replaceable from outside the base 32 without any disassembly. The airstream exits chamber 26 at the left moving across into the heat chamber 28, where it is heated by a finned electrical element and from which the airstream exits at pipe fitting 32A.

Typically the intake assembly 10 is mounted on top of a storage tank via four mounting legs 34 which may be configured as part of a mounting stand assembly supporting assembly 10 via base 32. Pipe fitting 32A is closely coupled to the intake of the storage tank (14 FIG. 1), either on top or at near the top at the intake end of the tank, opposite the outlet end of the tank. Electrical wiring and electronic control circuitry may be contained in a compartment located in region 36 of base 32.

The sterilizing system is typically designed to run continuously at a rate of 37 cubic feet/minute: this is necessary to maintain positive pressure above atmospheric pressure inside the tank 16 (FIG. 1) even at times when the fluid 16 in the tank is being depleted at a rate approaching 300 gallons/minute, otherwise negative pressure could potentially draw unsterile air into the tank through the outlet vent 12, The sterilizing system may include a remote control panel that includes indicator/warning lamps, e.g. five lamps as follows:

(1) red lamp marked "CHECK FILTER" indicates inadequate or no airflow e.g. due to filter(s) needing replacement, blower failure or main fuse blown.

(2) red lamp marked "CHECK LIGHT" indicates inadequate or no ultraviolet radiation e.g. due to UV lamp failure.

(3) green lamp marked "POWER ON" to verify presence of electric line power.

(4) red lamp marked "LOW HEAT" indicates inadequate or no heating, e.g. due to failed heater element, and (5) red lamp marked "HIGH HEAT" indicates excessive heat e.g. due to a defective thermostat.

An optional high level tank alarm may be provided, implemented by a modular hook-up.

All circuitry is GFI (ground fault indicator) and fuse-protected.

All lamps, ballast and blower motor service or replacement are completed without disturbing the sterile environment. All filters and lamps can be changed in less than five minutes.

The use of stainless steel throughout eliminates external environmental concerns and, along with avoidance of airflow restriction, reduces the potential of developing points of contamination internally.

Figures 4, 5:
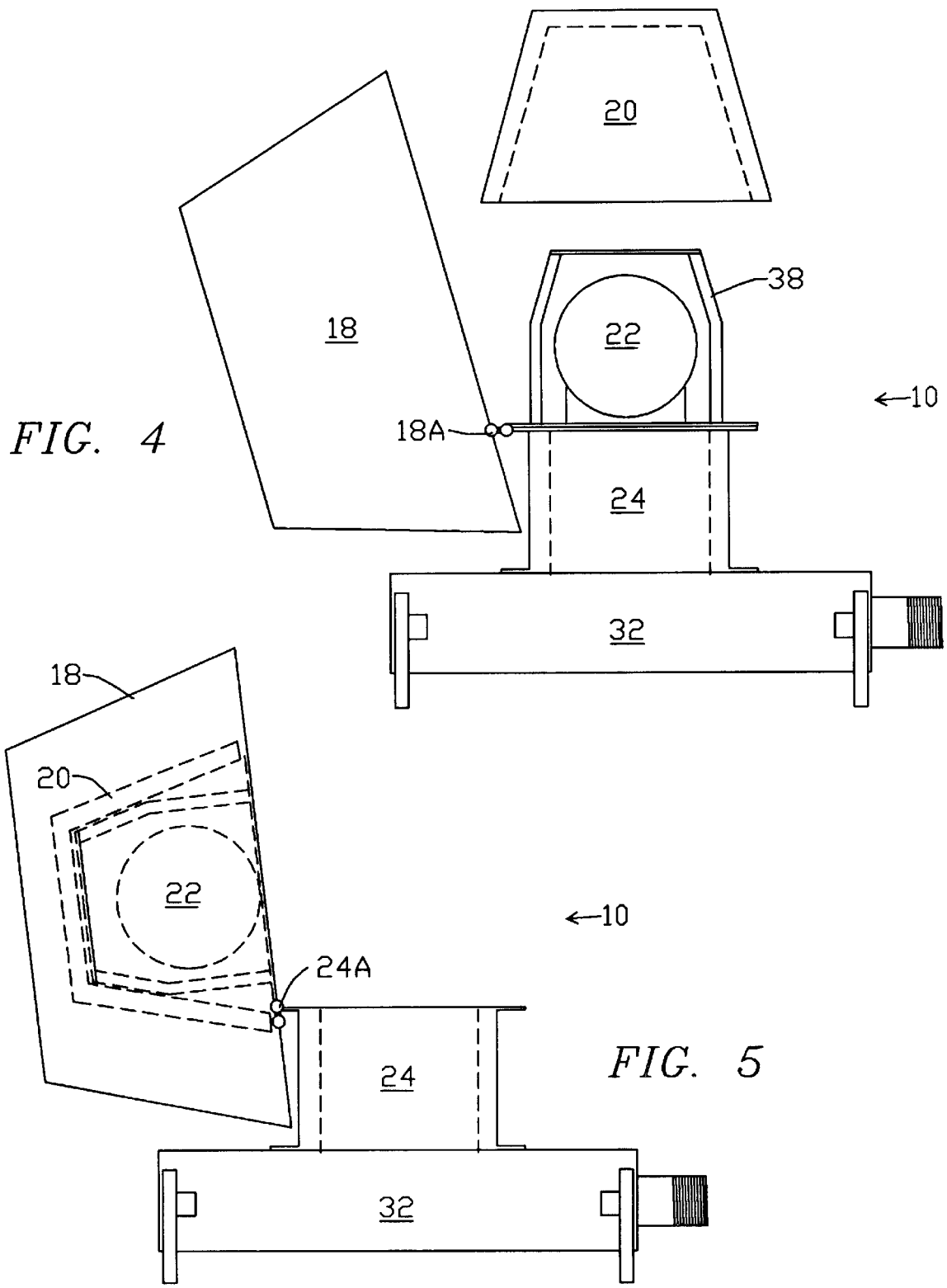
FIG. 4 is a side view as in FIG. 2, showing the hood hinged open and the intake filter removed upwardly.
FIG. 5 is a side view as in FIG. 4 with the blower assembly hinged open along with the hood for access to the main filter.

FIG. 4 is a side view as in FIG. 2, showing the hood 18 rotated at hinge 18A to provide access to the intake filter 20 which is shown removed upwardly away from the blower 22. A metal framework 38 is shaped to provide support inside the intake filter 20 in its working location surrounding blower 22 as in FIG. 2, while imposing minimal impedance to airflow.

FIG. 5 is a side view as in FIG. 4 with the blower 22 and its assembly pivoted to an open position at hinge 24A along with the hood 18 so as to provide access to the main filter 24, which can be removed by lifting upwardly, The intake filter 20 serves the dual important roles of protecting the blower 22 and its motor from air impurities and easing the burden of main filter 24, the invention could be practiced in a more basic manner without the intake filter 20.

When closed to the working position, hood 18 and the assembly including blower 22 are secured in place by locking draw poles of known art located at the side of housing of the main filter 24 housing opposite hinges 18A and 24A.

The invention may be practiced with the main component items (20, 22, 24, 26 and 28 FIG. 1) arranged in alternative locations other than those shown in FIGS. 2 and 3 as an illustrative preferred embodiment.

The invention may be embodied and practiced in other specific forms without departing from the spirit and essential characteristics thereof. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed is:

1. A method of forced ventilation with sterilized air for a storage tank containing liquid for human consumption and having an intake opening and an outlet opening, comprising the steps of:

(1) drawing air from surrounding atmosphere with an electric blower and thus producing a continuous primary air flow;

(2) directing the primary air flow through a main filter having a designated transmission size rating, thus producing a flow of filtered air;

(3) directing the flow of filtered air into an ultra-violet radiation chamber thus producing a flow of sterilized air;

(4) directing the flow of sterilized air through a heating chamber thus producing a flow of heated sterilized air; and (5) directing the flow of heated sterilized air into the storage tank via the intake opening thus purging foregoing air in the tank to exit via the outlet opening.

2. The method of forced ventilation with sterilized air as defined in claim 1 further comprising the preliminary step of (A1) filtering atmospheric air with an intake filter having a transmission size rating greater than that of the main filter, the intake filter being made and arranged to intercept all air drawn in by the blower.

3. The method of forced ventilation with sterilized air as defined in claim 2 further comprising the subsequent step of (6) providing an outlet vent comprising a length of pipe configured in an inverted U shape having a first end fitted to the outlet opening of the tank and having a second end fitted with a filter screen, made and arranged to minimize effects of weather and environmental disturbances while allowing substantially free passage of airflow from the tank.

4. The method of forced ventilation with sterilized air as defined in claim 1 further comprising the subsequent step of (6) providing a vent comprising a tubular duct configured in an inverted U shape having a first end fitted to the outlet opening of the tank and having a second end fitted with a filter screen, made and arranged to minimize effects of weather and environmental disturbances while allowing substantially free passage of airflow from the tank.

5. A forced air tank ventilating and sterilizing system for a storage tank containing liquid for human consumption and having an intake opening and an outlet opening, comprising;:

an electric blower made and arranged to continuously draw air from surrounding atmosphere and thus produce a continuous primary air flow;

a main filter having a designated transmission size rating, made and arranged to receive the primary air flow as input and to thus produce a flow of filtered air as output;

an ultra-violet radiation chamber equipped with a source of ultra-violet radiation, receiving as input the flow of filtered air from the main filter and thus producing a flow of filtered and sterilized air as output;

a heating chamber equipped with a source of heat, receiving as input the flow of filtered and sterilized air from the ultra-violet radiation chamber, and thus producing a flow of filtered, sterilized and heated air as output; and air coupling means coupling the heating chamber to the intake opening in the tank, whereby the flow of filtered, sterilized and heated air is caused to enter the tank and continuously purge foregoing air in the tank to exit via the outlet opening.

6. The forced air tank ventilating and sterilizing system as defined in claim 5 further comprising:

an intake filter, having a transmission size rating greater than that of the main filter, made and arranged to intercept all air drawn in by the blower.

7. The forced air tank ventilating and sterilizing system as defined in claim 6 further comprising:

a base housing portion containing the ultra-violet radiation chamber and the heating chamber, and configured with an air passage opening on a top surface thereof;

a main filter housing, mounted on top of the base housing portion in communication with the air passage opening, containing the intake filter, said blower and said main filter;

a blower assembly, mounted on top of the main filter housing, comprising said blower and said intake filter arranged in a functional manner; and a weather-protective hood surrounding the blower assembly on all sides and top thereof.

8. The forced air tank ventilating and sterilizing system as defined in claim 7 wherein the blower assembly and the weather-protective hood are each attached in a hinged manner along an upper edge of the main filter housing so as to facilitate maintenance and replacement of the intake filter and the main filter.

9. The forced air tank ventilating and sterilizing system as defined in claim 5 further comprising: an outlet vent configured in an inverted U shape having a first end fitted to the outlet opening of the tank and having a second end fitted with a filter screen, made and arranged to minimize effects of weather and environmental disturbances.

10. The forced air tank ventilating and sterilizing system as defined in claim 9 wherein the outlet vent comprises:

a tubular outer wall of aluminum;

a tubular inner wall of stainless steel; and a layer of thermal insulation disposed between the outer wall and the inner wall.

* * * * *